United States Patent [19]

Bedeschi et al.

[11] Patent Number: 5,362,740
[45] Date of Patent: Nov. 8, 1994

[54] DIHYDROBENZOFURAN CARBOXAMIDES AND PROCESS FOR THEIR PREPARATION

[75] Inventors: Angelo Bedeschi, Milan; Walter Cabri, Rozzano; Ilaria Candiani, Varese; Silvia De Bernardinis; Marcello Marchi, both of Novara; Mario Varasi, Milan, all of Italy

[73] Assignee: Farmitalia Carlo Erba S.r.l., Milan, Italy

[21] Appl. No.: 983,274

[22] Filed: Nov. 30, 1992

Related U.S. Application Data

[63] Continuation of Ser. No. 809,159, Dec. 18, 1991, abandoned.

[30] Foreign Application Priority Data

Dec. 27, 1990 [GB] United Kingdom ............... 9028104
Apr. 5, 1991 [GB] United Kingdom ............... 9107140

[51] Int. Cl.$^5$ ............... C07D 413/00; A61K 31/44
[52] U.S. Cl. ............... 514/299; 546/112; 546/126
[58] Field of Search ............... 546/112, 126; 514/299

[56] References Cited

U.S. PATENT DOCUMENTS

| | | | |
|---|---|---|---|
| 3,705,165 | 12/1972 | Sturm et al. | 546/112 |
| 4,350,691 | 9/1982 | Hadley et al. | 546/112 |
| 4,544,660 | 10/1985 | Hadley et al. | 546/112 |
| 4,921,982 | 5/1990 | Cohen et al. | 549/462 |
| 4,997,956 | 3/1991 | Lacefield | 549/15 |

Primary Examiner—Johann Richter
Assistant Examiner—Catherine S. Kilby Scalzo
Attorney, Agent, or Firm—Oblon, Spivak, McClelland, Maier & Neustadt

[57] ABSTRACT

A compound of formula (I)

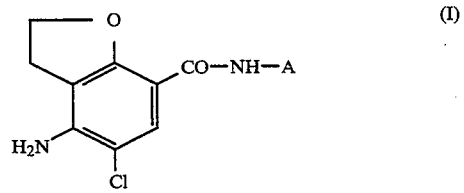

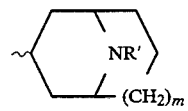

wherein R' is hydrogen or methyl, m is zero or 1 and the symbol means that the azabicyclic rings may be in the α or the β orientation, and the pharmaceutically acceptable salts thereof, are useful in treating CNS disorders, gut motility disorders, and/or emesis and/or pain in mammals, and/or migraine.

12 Claims, No Drawings

DIHYDROBENZOFURAN CARBOXAMIDES AND PROCESS FOR THEIR PREPARATION

This application is a continuation of application Ser. No. 07/809,159, filed on Dec. 18, 1991, now abandoned.

The present invention relates to new dihydrobenzofuran carboxamide derivatives, to a process for their preparation, and to pharmaceutical compositions containing them. The invention herein provides compounds of the formula (I)

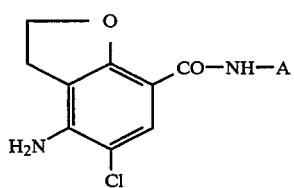

wherein A is a substituent selected from the group consisting of

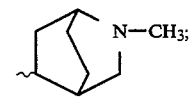 a)

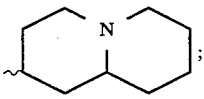 b)

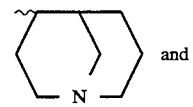 c) and

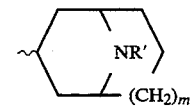 d)

wherein R' is hydrogen or methyl, m is zero or 1, and the symbol means that the azabicyclic ring may be in the α or the β orientation.

The invention includes also the pharmaceutically acceptable salts of the compounds of formula (I) as well as all the possible isomers covered by the formula (I), both separately and in mixture.

Preferably, in the above formula (I) the substituent A is in the a orientation.

Preferably when A is a group as defined above under d), R' is methyl and m is zero or 1.

Pharmaceutically acceptable salts of the compounds of formula (I) are their salts with suitable pharmaceutically acceptable acids, such as those with inorganic acids, e.g. hydrochloric or sulfuric acid, or with organic acids such as organic carboxylic acids, e.g., citric, tartaric, fumaric and the like, or organic sulfonic acids, e.g., methanesulfonic or ethanesulfonic acid. Particularly preferred salts are the hydrochlorides. Preferred compounds according to the invention are the compounds of formula (I) wherein A is a group as defined above under d).

Specific examples of compounds of formula (I) are the following ones, either in the β or in the α configuration, preferably in the α configuration:

1) 4-amino-5-chloro-N-(8-methyl-8-azabicyclo[3.2.1]oct-3-yl)-2,3-dihydrobenzo[b]furan-7-carboxamide;
2) 4-amino-5-chloro-N-(9-methyl-9-azabicyclo[3.3.1]non-3-yl)-2,3-dihydrobenzo[b]furan-7-carboxamide;
3) 4-amino-5-chloro-N-(1-azabicyclo[4.4.0]dec-4-yl)-2,3-dihydrobenzo[b]furan-7-carboxamide;
4) 4-amino-5-chloro-N-(1-azabicyclo[3.3.1]non-4-yl)-2,3 dihydrobenzo[b]furan-7-carboxamide;
5) 4-amino-5-chloro-N-(2-methyl-2-azabicyclo[2.2.2]oct-5-yl)-2,3-dihydrobenzo[b]furan-7-carboxamide;

and the pharmaceutically acceptable salts thereof, especially the hydrochlorides.

The structural formulae of the above listed compounds, according to their progressive number, are the following:

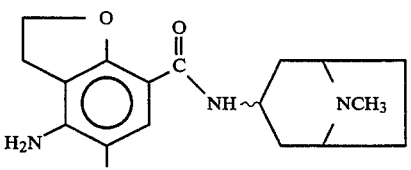 1)

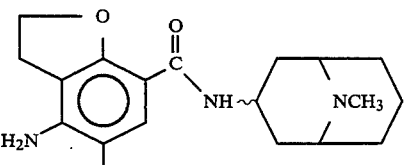 2)

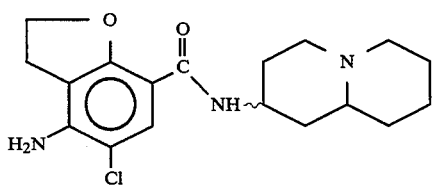 3)

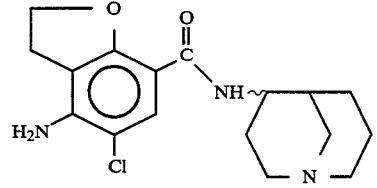 4)

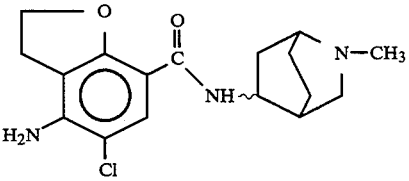 5)

In the present specification, anywhere a formula has a substituent with a symbol , the formula may represent a compound having the azabicyclic ring only in the α orientation or only in the β orientation or the formula may represent a mixture of both compounds having the azabicyclic ring in the α orientation and compounds having azabicyclic ring in the β orientation.

The compounds of the invention are prepared by a process comprising:
reacting a compound of formula (II),

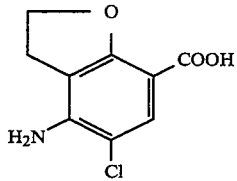

or a reactive derivative thereof, with a compound of formula (III)

$$H_2N-A \qquad (III)$$

wherein A is as defined above and, if desired, salifying a free compound of formula (I) or obtaining a free compound of formula (I) from a salt thereof and/or, if desired, separating a mixture of isomers of a compound of formula (I) into the single isomers.

A reactive derivative of the compound of formula (II) may be, e.g., a corresponding $C_1$-$C_4$ alkyl ester, a corresponding halide, in particular the chloride, or the mixed anhydride with an appropriate carboxylic acid.

A preferred mixed anhydride is that obtained reacting a compound of formula (II) with ethylchloroformate.

The reaction between a compound of formula (II), or a reactive derivative thereof, and a compound of formula (III), may be carried out according to the known methods described in the organic chemistry for the amidation reactions following conventional procedures, for example as described in U.S. Pat. No. 4,888,353.

In particular the reaction between the compound of formula (II) and the compound of formula (III) may be, e.g., carried out in an inert, preferably anhydrous, organic solvent such as, for example, dimethylformamide, in the presence of a condensing agent, e.g. N,N-carbonyldiimidazole, according to conventional procedures.

The optional salification of a free compound of formula (I), the optional preparation of a free compound of formula (I) from a salt thereof, and the optional separation of a mixture of isomers of formula (I) into the single isomers, may be carried out in a conventional way, following the known and usual procedures of the organic chemistry.

The compound of formula (II) is a known compound and may be prepared by known methods, e.g. those described in U.S. Pat. No. 4,888,353.

The compounds of formula (III) are known compounds too and may be prepared by known methods.

For example, a compound of formula (III) wherein the group A is endo-8-methyl-8-azabicyclo[3.2.1]oct-3-yl, i.e. the compound endo-8-methyl-8-azabicyclo[3.2.1]octan-3-amine, may be prepared following the procedure described in Archer S., Lewis T., Unser M., J. Am. Chem. Soc. 1987, 79, 4194; and a compound of formula (III) wherein the group A is endo-9-methyl-9azabicyclo[3.3.1]non-3-yl, i.e. the compound endo-9-methyl-9azabicyclo[3.3.1]nonan-3-amine, may be prepared following the procedure described in Hadley M., EP 13.138, 1979; Chem. Abstract 1981, 94, 65477; or Donatch P., Engel G., Uegi B. Richardson B., Stadler P., GB 2,125,398, 1984.

The compounds of formula (I) are 5HT3 receptor antagonists, as proved for example by the fact that they have been found to be active in antagonizing the Bezold-Jarisch chemoreflex evoked by 5-HT in the anesthetised rat according to the method described by Cohen M. L. et al., J. Pharmacol. Esp. Ther. 248, 197–201 (1989).

The following Table I reports the in vivo 5HT3 antagonist activity data obtained in this test for the compounds of the invention 4-amino-5-chloro-N-(9-methyl-9-azabicyclo[3.3.1]non-3-yl)-2,3-dihydrobenzo[b]furan-7-carboxamide (internal code FCE 27270) and 4-amino-5-chloro-N-(8-methyl-8-azabicyclo[3.2.1]oct-3-yl)-2,3-dihydrobenzo[b]furan-7-carboxamide (internal code FCE 27271) in comparison with the known reference compound Ondansetron, namely (±)-1,2,3,4-tetrahydro-9-methyl-3-(2-methylimidazol-1-yl-methyl)-carbazol-4-one.

The data in Table I clearly show that the tested compounds of the invention have, as 5HT3 receptor antagonists, a greatly superior activity over the reference.

TABLE I

Inhibition of the Bezold-Jarisch reflex elicited by 5-HT (20 μg/kg I.V.) by I.V. FCE 27270, FCE 27271 and ondansetron in the anesthetized rat.
Values are mean ± S.E.M. from 6 animals

| Compound | Dose (μg/kg I.V.) | % inhibition | $ED_{50}$ (μg/kg) (limits) |
|---|---|---|---|
| FCE 27270 | 0.1 | 37.25 ± 2.77* | |
| | 0.3 | 54.09 ± 3.39* | 0.20 |
| | 1 | 89.11 ± 3.39* | (0.14–0.26) |
| FCE 27271 | 0.1 | 23.83 ± 5.50* | |
| | 0.3 | 55.69 ± 4.05* | 0.81 |
| | 1 | 82.54 ± 2.33* | (0.60–1.07) |
| Ondansetron | 1 | 32.86 ± 8.58* | |
| | 3 | 58.42 ± 3.89* | 2.25 |
| | 10 | 81.21 ± 1.82* | (1.61–2.95) |
| Vehicle | — | 1.55 ± 4.01 | — |

*p < 0.01 vs controls (Dunnett's test)

The compounds of the invention have also been found to be potent and selective inhibitors of the binding of $^3$H-GR65630 (a selective 5-HT3 receptor antagonist) according to the method described by Kilpatrick G. J. et al., Nature, 330, 746–748 (1987).

The following Table II reports the data obtained in this in vitro test for the compounds of the invention FCE 27270 and FCE 27271 in comparison with the known reference compounds Ondansetron, MDL 72222 and Metoclopramide.

MDL 72222 is the compound of formula

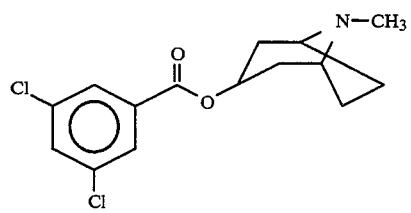

GR 65630 is the compound of formula

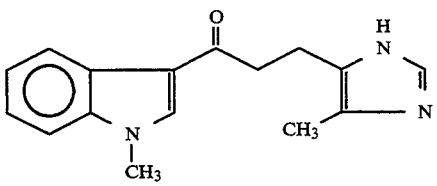

For Metoclopramide see Merck Index 10th Edition 6019, page 880.

TABLE II

| 5-HT$_3$ binding affinity$^{(a)}$ for rat entorhinal cortex | | |
|---|---|---|
| | Ki (nM) | |
| Compound | high | low |
| FCE 27270 | 0.092 | 38.960 |
| FCE 27271 | 0.833 | 96.200 |
| Ondansetron | 1.98 | 406.7 |
| MDL 72222 | 25.5 | — |
| Metoclopramide | 547 | — |

$^{(a)}$[$^3$H]-GR 65630 labeled 5-HT$_3$ sites.

The tested compounds were able to interact with 5-HT$_3$-serotonin receptors labeled in the entorhinal cortex of the rat brain with $^3$H-GR 65630. Of these FCE 27270, 27271 and Ondansetron interacted according to a two site non-linear fitting model, while MDL 72222 and Metoclopramide displaced $^3$H-GR 65630 according to one site non-linear fitting: this is the reason why only one (rather than two) Ki value is reported in Table II for the latter two compounds.

The tabulated data clearly show a superior activity of the compounds of the invention over the references.

In view of the said activities, the compounds of the present invention can be useful, for example, in the treatment of CNS disorders such as, e.g., anxiety and psychosis, and/or in the treatment of gut motility disorders, and/or emesis.

In view of the above activities the compounds of the invention can be also useful as, for example, anti-migraine or anti-drug addiction agents, or as cognition activators.

The present compounds have further been found to have utility as analgesics. The analgesic activity of the compounds of the invention has been shown, e.g., by the fact that they have proved to be active in the formalin-induced inflammatory pain test described by Dubuisson and Dennis in: "The formalin test: a quantitative study of analgesic effects of morphine, meperidine and brainstem stimulation in rats and cats" (Pain 4, 161, 1977).

In view of their analgesic properties the compounds of formula (I) can be useful, e.g., in the treatment of pain in mammals, e.g., in the treatment of some forms of inflammatory pain in humans.

The compounds of the invention may be administered in a variety of dosage forms, e.g., orally in the form of tablets, pills, capsules, suspensions, drops or syrups; parenterally, e.g., intravenously, intramuscularly as solutions or suspensions, or by subcutaneous administration.

The pharmaceutical compositions containing the compounds of the invention may be prepared in a conventional way by employing conventional carriers or diluents.

Conventional carriers or diluents are, for example, water, gelatine, lactose, starches, magnesium stearate, talc, vegetable oils, cellulose and the like.

Tablets, pills and capsules may, e.g., contain a binder such as, e.g., gum tragacanth; excipients such as, e.g., dicalcium phosphate; a disintegrating agent such as, e.g., corn starch, a lubricant such as, e.g., magnesium stearate; a sweetening agent such as, e.g., sucrose or a flavouring agent such as cherry flavouring.

Suitable pharmaceutical forms for parenteral use are sterile aqueous solutions or dispersions and sterile powders for the extemporaneous preparations.

The dosage of the present compounds, either for prophylaxis or therapeutic treatment, will depend on the chosen route of administration, on the particular compound chosen, on the particular patient under treatment and also on the nature and severity of the disorder.

A suitable therapeutically effective dosage may be, for example, included within the range of from about 0.01 to about 20 mg/kg of body weight.

Preferably the compounds may be, e.g., administered in single or divided doses such that the total daily dosage falls within the range of about 0.02 to about 10 mg/kg per day.

The following examples illustrate the preparation of the compounds of the present invention. These examples are illustrative only and are not intended to limit the scope of the invention in any way.

EXAMPLE 1

4-amino-5-chloro-N-(endo-8-methyl-8-azabicyclo[3.2.1]oct-3-yl)-2,3-dihydrobenzo[b]furan-7-carboxamide.HCl To a stirred solution of 4-amino-5-chloro-2,3-dihydrobenzo[b]furan-7-carboxylic acid (2.13 g; 0.010 mole) in 30 ml of anhydrous dimethylformamide is added N,N-carbonyldiimidazole (1.96 gr; 0.012 mole).

Nitrogen is bubbled into the solution and stirring at room temperature continued overnight, followed by dropwise addition of a solution of endo-8-methyl-8-azabicyclo[3.2.1]octan-3-amine, (1.40 g; 0.010 mole), in 5 ml of anhydrous dimethylformamide. The reaction mixture is heated at 70° C. for 18 hours, cooled, poured into water and extracted with methylene chloride. The organic layer is washed twice with a sodium bicarbonate solution and dried over anhydrous sodium sulfate. The solution is filtered, evaporated to dryness and the product purified by flash-chromatography (SiO$_2$)(CH$_2$Cl$_2$—MeOH—NH$_4$OH 30% 80:20:1, as eluant), followed by treatment with a solution of hydrochloric acid in ethanol: the solid obtained is recovered by filtration and recrystalised in ethanol to yield 1.6 g. of the title product; m.p. 290°–300° C. (dec.).

EXAMPLE 2

The following compounds can also be prepared from the corresponding carboxylic acid and the appropriate amine according to the procedure of example 1:

4-amino-5-chloro-N-(endo-9-methyl-9-azabicyclo[3.3.1]non-3-yl)-2,3-dihydrobenzo[b]furan-7-carboxamide.HCl, m.p. 260°–280° C. (dec.);

4-amino-5-chloro-N-(1-azabicyclo[4.4.0]dec-4-yl)-2,3-dihydrobenzo[b]furan-7-carboxamide.HCl;

4-amino-5-chloro-N-(1-azabicyclo[3.3.1]non-4-yl)-2,3-dihydrobenzo[b]furan-7-carboxamide.HCl; and 4-amino-5-chloro-N-(2-methyl-2-azabicyclo[2.2.-
2]oct-5-yl)-2,3-dihydrobenzo[b]furan-7-carbox-
amide.HCl.

EXAMPLE 3

Tablets each weighing 150 mg and containing 60 mg of the active substance can be manufactured by blending and compressing the following ingredients:

| | |
|---|---|
| 4-amino-5-chloro-N-(endo-8-methyl-8-azabicyclo[3.2.1]oct-3-yl)-2,3-dihidrobenzo[b]furan-7-carboxamide hydrochloride | mg 60 |
| Starch | mg 50 |
| Cellulose microcrystalline | mg 30 |
| Polyvinylpyrrolidone | mg 5 |
| Sodium carboxymethyl starch | mg 4,5 |
| Magnesium stearate | mg 0.5 |

EXAMPLE 4

Capsules, each dosed at 200 mg and containing 80 mg of the active substance can be prepared as follows:

| | |
|---|---|
| 4-amino-5-chloro-N-(endo-8-methyl-8-azabicyclo[3.2.1]oct-3-yl)-2,3-dihydrobenzo[b]furan-7-carboxamide hydrochloride carboxamide hydrochloride | mg 80 |
| Corn starch | mg 60 |
| Cellulose Microcrystalline | mg 59 |
| Magnesium stearate | mg 1 |

This formulation can be encapsulated in two-piece hard gelatin capsules and dosed at 200 mg for each capsule.

We claim:

1. A compound of formula (I)

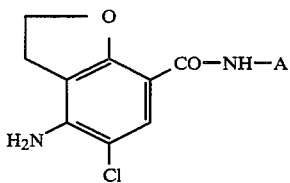

wherein A is

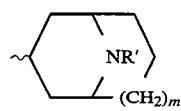

wherein R' is hydrogen or methyl, m is zero or 1 and the symbol φ means that the azabicyclic rings may be in the α or the β orientation, or a pharmaceutically acceptable salt thereof.

2. A compound of formula (I) according to claim 1 wherein the group A is in the α orientation, or a pharmaceutically acceptable salt thereof.

3. A compound of formula (I) or salt thereof according to claim 1 selected from the group consisting of:
   4-amino-5-chloro-N-(endo-8-methyl-8-azabicyclo[3.2.1]oct-3-yl)-2,3-dihydrobenzo[b]furan-7-carboxamide; and
   4-amino-5-chloro-N-(endo-9-methyl-9-azabicyclo[3.3.1]non-3-yl)-2,3-dihydrobenzo[b]furan-7-carboxamide;
or a pharmaceutically acceptable salt thereof.

4. A salt of a compound of formula (I) according to claim 3, wherein the salt is the hydrochloride.

5. A pharmaceutical composition containing a suitable carrier and/or diluent and, as the active principle, a compound of formula (I) as defined in any of claims 1, 2 or 3, or a pharmaceutically acceptable salt thereof.

6. A method of treating a CNS disorder comprising administering to a patient in need thereof an effective amount of the compound of claim 1, or a pharmaceutically acceptable salt thereof.

7. A method according to claim 6, wherein said CNS disorder is selected from the group consisting of anxiety and psychosis.

8. A method of treating pain in a mammal, comprising administering to a mammal in need thereof an effective amount of the compound of claim 1, or a pharmaceutically acceptable salt thereof.

9. A method of treating a gut motility disorder, emesis, or migraine, comprising administering to a patient in need thereof an effective amount of the compound of claim 1, or a pharmaceutically acceptable salt thereof.

10. A method according to claim 6, wherein the group A, in formula (I) or the pharmaceutically acceptable salt thereof, is in the α orientation.

11. A method according to claim 8, wherein the group A, in formula (I) or the pharmaceutically acceptable salt thereof, is in the α orientation.

12. A method according to claim 9, wherein the group A, in formula (I) or the pharmaceutically acceptable salt thereof, is in the α orientation.

* * * * *

UNITED STATES PATENT AND TRADEMARK OFFICE
CERTIFICATE OF CORRECTION

PATENT NO. : 5,362,740
DATED : NOVEMBER 8, 1994
INVENTOR(S) : ANGELO BEDESCHI ET AL

It is certified that error appears in the above-identified patent and that said Letters Patent is hereby corrected as shown below:

On the title page, item:

No. [57] ABSTRACT, second line below formula (1), after "symbol", insert --  --.

Column 1, line 47, after "symbol", insert --  --;
line 54, after "the", insert --α--.

Column 2, line 65, after "symbol", insert --  --.

Column 4, line 11, delete "5HT3" and insert --$5HT_3$--.

UNITED STATES PATENT AND TRADEMARK OFFICE
CERTIFICATE OF CORRECTION

PATENT NO. : 5,362,740
DATED : November 8, 1994
INVENTOR(S) : Angelo Bedeschi, et al.

It is certified that error appears in the above-indentified patent and that said Letters Patent is hereby corrected as shown below:

Column 8, line 9, after "symbol", insert --  --;
line 18, delete "[3.2.11oct-3-yl)" and insert
--[3.2. 1]oct-3-yl)--.

Signed and Sealed this

Eleventh Day of July, 1995

Attest:

BRUCE LEHMAN

*Attesting Officer*  *Commissioner of Patents and Trademarks*